United States Patent
Marinelli

(10) Patent No.: US 6,958,430 B1
(45) Date of Patent: Oct. 25, 2005

(54) DISPOSABLE ABSORBENT ARTICLE COMPRISING EXPANDABLE FIBERS AND BEING CAPABLE OF SELF-SHAPING IN USE

(75) Inventor: Luigi Marinelli, Pescara Via Aterno (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/180,005

(22) PCT Filed: Apr. 28, 1997

(86) PCT No.: PCT/US97/07139

§ 371 (c)(1),
(2), (4) Date: May 6, 1999

(87) PCT Pub. No.: WO97/40795

PCT Pub. Date: Nov. 6, 1997

(30) Foreign Application Priority Data

Apr. 29, 1996 (EP) ............................. 96106720

(51) Int. Cl.$^7$ ................................. A61F 13/15
(52) U.S. Cl. ................. 604/375; 604/365; 604/377; 604/379; 604/385.01; 604/385.04; 604/387
(58) Field of Search ............... 604/368, 369, 604/371–380, 383, 385.1, 386–387, 389–390, 365, 385.01, 385.12, 385.16, 385.04

(56) References Cited

U.S. PATENT DOCUMENTS

| | | | | |
|---|---|---|---|---|
| 3,848,598 A | * | 11/1974 | Mesek | 604/374 |
| 3,954,493 A | * | 5/1976 | Battista et al. | |
| 4,041,950 A | * | 8/1977 | Jones, Sr. | 604/375 |
| 4,057,061 A | * | 11/1977 | Ishikawa et al. | 604/375 |
| 4,919,681 A | * | 4/1990 | Tyler et al. | 604/375 |

* cited by examiner

*Primary Examiner*—John G. Weiss
*Assistant Examiner*—Kim Reichle
(74) *Attorney, Agent, or Firm*—Theodore P. Cummings; Kevin C. Johnson; Matthew P. Fitzpatrick

(57) ABSTRACT

A substantially flat disposable absorbent article for wearing adjacent a body discharge area having a longitudinal centerline, and a lateral centerline orthogonal thereto, and defining longitudinal and lateral directions respectively. The disposable absorbent article includes a liquid pervious top sheet, a back sheet joined to the top sheet, and an absorbent core intermediate the back sheet and the top sheet. The absorbent core includes a layer of compressed, cellulose based, linear fibers for expanding the article into a tridimensional structure while being worn by a user. The layer of compressed, cellulose based, linear fibers is activated by body fluids.

7 Claims, 2 Drawing Sheets

DISPOSABLE ABSORBENT ARTICLE COMPRISING EXPANDABLE FIBERS AND BEING CAPABLE OF SELF-SHAPING IN USE

FIELD OF THE INVENTION

The present invention relates to disposable absorbent articles. Disposable absorbent articles are considered to be absorbent devices designed to be worn externally of the body by a user and to receive fluids discharged from the body. In particular the present invention relates to substantially flat disposable absorbent sanitary napkins, catamenials, incontinence inserts, pantiliners and diapers comprising a layer of compressed fibres for expanding the article into a tridimensional structure while being worn by a user. The layer of compressed fibres is activated by body fluids and provides the article with a self-shaping capability during the use.

BACKGROUND OF THE INVENTION

In their basic form, disposable absorbent articles comprise an absorbent core interposed between a pervious body-contacting element (alternatively referred to as a topsheet or an overwrap) and an impervious protective barrier (alternatively referred to as a backsheet). The absorbent element is, of course, intended to receive and contain the fluids discharged from the body. The body-contacting element is intended to provide comfortable and dry-feeling contact with body surfaces while allowing free passage of fluids therethrough into the absorbent element. The protective barrier is intended to prevent the fluids which are expelled or which escape from the absorbent element from soiling the user's garments.

In addition to the three functional elements mentioned above, disposable absorbent articles are generally provided with means for supporting the device adjacent the user's crotch area, even as the user moves, where it can most effectively perform its intended function. Typically, absorbent articles as sanitary napkins are provided with an adhesive attachment means for securing the device to the inner crotch area of the user's undergarments.

Improved fluid interception can occur if the absorbent article is in close contact with the body of the wearer.

While previously known absorbent articles perform their intended function, each conventional design can be further improved in one or more of absorbency of body fluids, protection of the user's garments from soiling, and/or physical comfort to the user.

With respect to disposable sanitary napkins several attempts have been made in the art to improve body contact with the wearer, and hence absorb fluids upon discharge and thereby minimize soiling by providing a sanitary napkin having an anatomically shaped configuration, particularly including those that are raised upwardly or humped in their medial portions so as to be near or in contact with the pudendal region when worn.

On female users these sanitary napkins attempt to contact and absorb menses immediately as it leaves the vestibule.

Some articles have been also described in which an anatomically shaped configuration is provided during the wearing time, with the advantage of a better fit to the anatomy.

According to U.S. Pat. No. 3,512,530 a sanitary napkin is described in which a compressed regenerated cellulose sponge layer is combined with a larger fibrous cellulose layer to form a multiple ply absorbent core. The compressed regenerated cellulose sponge layer is positioned over the fibrous layer, and it is typically centered about it; it is intended as the primary absorbent element of the sanitary napkin, while the fibrous layer acts as a secondary or back up absorber.

The sanitary napkin may be therefore very thin prior to use, as compared to other sanitary products having the same absorbent capacity.

Although the compressed regenerated cellulose sponge layer is capable of expanding in Z-direction upon fluid absorption, the structure described is not particularly suitable to provide an effective body contact with the wearer's anatomy and might cause discomfort to the user due to the characteristics of the compressed regenerated cellulose sponge material, particularly when it is dry.

EP Patent 293 208 B1 describes the use of multiple layers of compressed regenerated cellulose sponge sheets in a sanitary napkin as the sole absorbent material instead of the usual cellulose pulp absorbent core in order to obtain an absorbent article of improved strength and shape retainability in wet conditions, as compared to traditional absorbent articles with fluff cores that tend to be broken or to form lumps in use.

The sheets are provided with slits in order to enhance their flexibility, with a better comfort for the user, and to increase the fluid absorbing area.

The sanitary napkin described in the EP patent 293 208 B1 has a structure that is not specifically intended to provide a self shaping capability during the use taking advantage of the swelling of the absorbent material, but rather a better strength when wetted than articles using conventional, fluff-based absorbent cores, and a better flexibility and absorbency rate as compared to articles using the same compressed regenerated cellulose sponge material.

U.S. Pat. No. 3,736,931 discloses a sanitary napkin having an outer non-compressed layer of fluid absorbent material and an inner core of highly compressed fluid absorbent material which is at least partially enclosed therein. The napkin preferably is V-shaped in cross section and is arch-shaped in its longitudinal direction by die compression. When the napkin is worn the fluid directs first into the inner compressed layer so as to cause it to swell and to expand the outer non-compressed layer in all directions, thereby adjusting itself to each wearer.

The sanitary napkin expands upon fluid absorption and may adjust itself to the user's anatomy, but since it is not flat prior to use it may be cumbersome to package and to handle; moreover, the expansion takes place mainly in the lateral direction, thus achieving an effective seal against the inner side of the thighs and at both sides of the vaginal orifice; therefore the structure is neither capable of forming a convex upward configuration nor does it bring the absorbent element in direct contact with the point of release of the fluid.

Therefore there is still the need for an absorbent article capable of providing an anatomically shaped configuration for a closer body contact which is achieved during the use upon activation by absorbed body fluids, while it is comfortable for the wearer and easy to produce and to package.

SUMMARY OF THE INVENTION

The present invention relates to disposable absorbent articles for wearing adjacent a body discharge area which are substantially flat prior to use. The substantially flat disposable absorbent article has a longitudinal centreline and a lateral centreline orthogonal thereto that define longitudinal and lateral directions respectively and a Z-direction which is orthogonal to both of them. The disposable absorbent article comprises a liquid pervious topsheet, a backsheet, preferably liquid impervious, joined to said topsheet, and an absorbent core intermediate the topsheet and the backsheet. The term "substantially flat", as used herein, refers to articles which have their main extension in one plane in contrast to being shaped. The absorbent core comprises a layer of compressed, regenerated cellulose, linear fibres capable of expanding the article into a tridimensional structure while being worn by a user and having a dry density of from 0.1 g/cc to 0.4 g/cc, wherein the layer of compressed fibres is activated by body fluids and has a thickness of between 2 mm to 7 mm.

BRIEF DESCRIPTION OF THE DRAWINGS

While the specification concludes with claims particularly pointing out and distinctly claiming the present invention, it is believed that the present invention will be better understood from the following description in conjunction with the following drawings:

DETAILED DESCRIPTION OF THE INVENTION

This invention relates to a disposable absorbent article which exhibits absorbency for bodily fluids, the protection of the user's garments from soiling, improved physical comfort to the user, and which is easy to produce and to package. The disposable absorbent article is described below by is reference to a sanitary napkin or catamenial. The term "sanitary napkin", as used herein, refers to an article which is worn by females adjacent to the pudendal region and which is intended to absorb and contain the various fluids which are discharged from the body (e.g., vaginal discharges, menses, and/or urine) and which is intended to be discarded after a single use. The disposable absorbent article is substantially flat prior to use.

The term "substantially flat", as used herein, refers to articles that have their main extension in one plane in contrast to being shaped. In a preferred embodiment a substantially flat article will have an absorbent core of constant thickness or, at least, will have an absorbent core that is not shaped in a direction which is orthogonal to the absorbent core itself. This does not exclude a general curvature of the absorbent core. It will be apparent to the man skilled in the art to which extent products can deviate from absolute flat shape and still benefit from the during the use shaping according to the present invention.

Sanitary napkins with longitudinal side cuffs, which may be optionally elasticated, and sanitary napkins with a moderate curvature are therefore within the scope of the present invention, provided that their absorbent core is not shaped prior to use in a direction that is orthogonal to the absorbent core itself.

The term "use", as used herein, refers to the period of time that starts when the absorbent article is actually put in contact with the anatomy of the user.

The terms "joined" or "affixed", as used herein, encompasses configurations whereby a first member is directly connected to a second member and configurations whereby a first member is indirectly connected to a second member by connecting the first member to intermediate members which in turn are connected to the second member.

Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
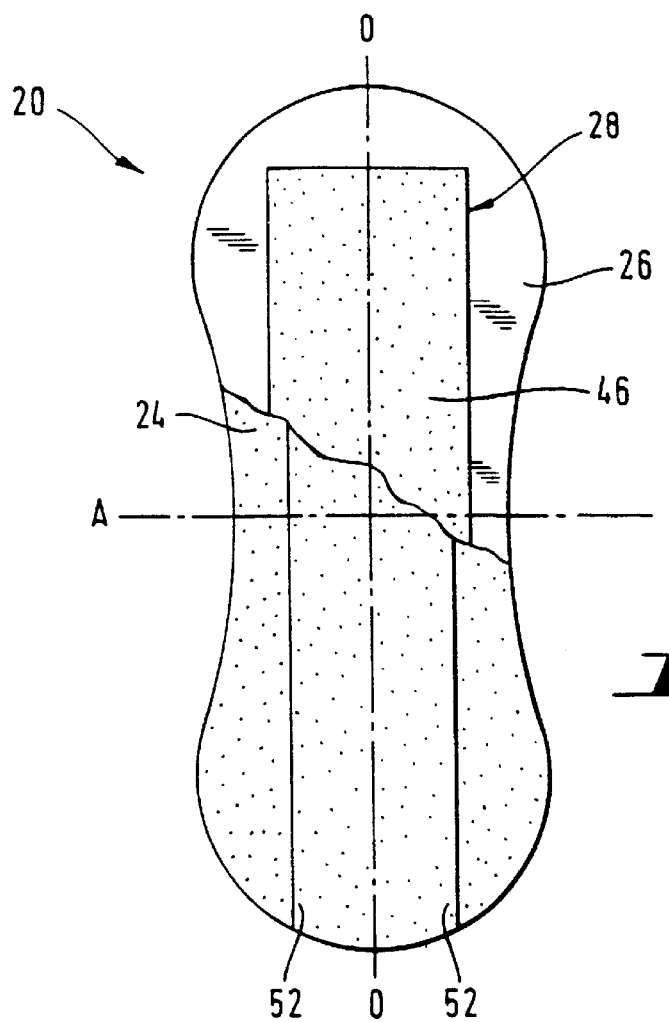
FIG. 1 is a top plan view, with portions cut-away of one embodiment of a sanitary napkin according to the present invention.
Figure 2:
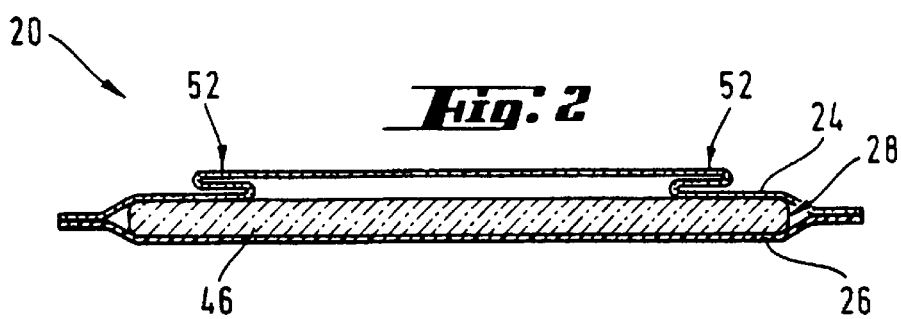
FIG. 2 is a cross-sectional view of the sanitary napkin shown in FIG. 1 as taken along a section line corresponding to the transverse centreline A—A.

In FIGS. 1 and 2, one preferred embodiment of a sanitary napkin 20 of the present invention is shown. FIG. 1 is a plan view of the sanitary napkin 20 of the present invention in its flat-out state prior to use with portions of the structure being cut-away to more clearly show the construction of the sanitary napkin 20 and with the portion of the sanitary napkin 20 which faces or contacts the wearer oriented towards the viewer. As shown in FIGS. 1 and 2, the sanitary napkin 20 preferably comprises a liquid pervious topsheet 24, a liquid impervious backsheet 26 joined to the topsheet 24, and an absorbent core 28 intermediate the topsheet 24 and the backsheet 26 comprising a layer of compressed fibres 46 for expanding the sanitary napkin into a tridimensional structure while being worn by a user.

The sanitary napkin 20 has two surfaces, a body contacting or facing surface, and a garment facing or contacting surface. The absorbent core 28 has corresponding body facing and garment facing surfaces. The sanitary napkin 20 has two centrelines, a longitudinal centreline O—O and a transverse centreline A—A orthogonal thereto. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral", as used herein, are interchangeable, and refer to a line, axis, or direction which lies within the plane of the sanitary napkin 20 and is generally perpendicular to the longitudinal direction. The Z-direction is orthogonal to both the longitudinal and lateral directions of the sanitary napkin 20 and extends outwardly from the plane of the sanitary napkin 20, which is defined by the longitudinal centreline O—O and the lateral centreline A—A. The term "longitudinally oriented" refers to a direction ±45 degrees of the longitudinal direction in the plane of the sanitary napkin 20; the term "laterally oriented" refers similarly to any other direction in the plane of the sanitary napkin 20.

The long edges of the sanitary napkin 20, which are aligned with the longitudinal centreline O—O, are the longitudinal side margins of the sanitary napkin 20. The ends of the sanitary napkin 20 joining the longitudinal side margins are the transverse ends of the sanitary napkin 20. Collectively the longitudinal side margins and transverse ends of the sanitary napkin 20 define its periphery. Similarly, the absorbent core 28 of the sanitary napkin 20 has a periphery defined by alternatively disposed longitudinal side margins and transverse ends.

Tridimensional structures of the sanitary napkin 20 are those in which the sanitary napkin structure is caused to expand, at least partially, in the Z-direction, in order to more closely conform to the user's anatomy. Said expansion preferably takes place in a direction that goes from the garment facing surface towards the body facing surface of the sanitary napkin 20. Particularly preferred are tridimensional structures with a convex upward configuration that are inclusive of, but not limited to, inverted U-shapes or inverted V-shapes. With these configurations the cross-sectional contour of the central portion of the sanitary napkin more closely matches the labia of the typical wearer.

The topsheet 24 is compliant, soft feeling, and non-irritating to the wearer's skin. Further, the topsheet 24 is liquid pervious, permitting liquid to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibres (e.g., wood or cotton fibers), synthetic fibres (e.g., polymeric fibres such as polyester, polypropylene, or polyethylene fibres); or from a combination of natural and synthetic fibres.

A preferred topsheet comprises an apertured formed film. Apertured formed films are preferred for the topsheet because they are pervious to body fluids and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. A preferred topsheet for the absorbent article of the present invention is a formed film described in one or more of the above patents and marketed on sanitary napkins by The Procter & Gamble Company of Cincinnati, Ohio as DRI-WEAVE.

In a preferred embodiment of the present invention, the body or exposed surface of the formed film topsheet is hydrophilic so as to help liquid transfer through the topsheet faster than if the body surface were not hydrophilic so as to diminish the likelihood that menstrual fluid will flow off the topsheet rather than flowing into and being absorbed by the absorbent core.

The topsheet of the present invention must be capable of expanding as the sanitary napkin 20 expands in a tridimensional structure upon absorption of body fluids. This may be achieved when the topsheet is made of a material that is intrinsically extensible under the forces exerted by the expanding layer of compressed fibres 46. In a preferred embodiment illustrated in FIGS. 1 and 2 the topsheet 24 is provided with two pleats or folds 52 symmetrically positioned at both sides of the longitudinal centreline O—O and substantially parallel to it. As shown in FIG. 2 the topsheet 24 in each pleat or fold 52 is folded twice on itself toward the longitudinal side margins of the sanitary napkin 20. A single pleat or fold or, alternatively, more than two folds may be also comprised in the topsheet 24 without departing from the scope of the present invention; the pleats or folds may be generally longitudinally or laterally oriented.

Figure 3:
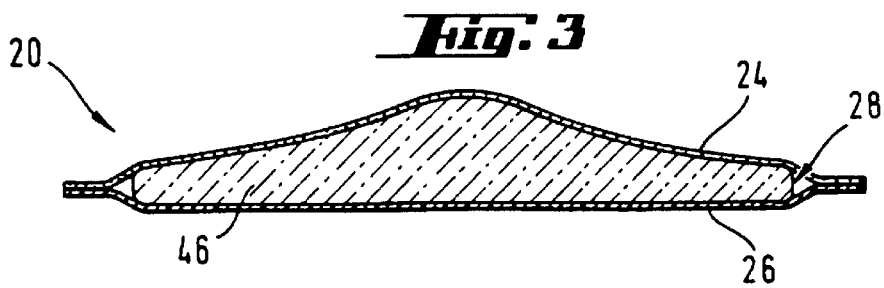
FIG. 3 is a cross-sectional view similar to that of FIG. 2, showing the sanitary napkin expanded into a tridimensional structure after activation during wear.

In a preferred embodiment illustrated in FIGS. 1 to 3 absorbent core 28 is entirely constituted by the layer of compressed fibres 46.

Alternatively, the absorbent core 28 can also comprise a further, substantially non expanding absorbent element.

The further, substantially non expanding absorbent element of the absorbent core 28 may be any absorbent means which is generally compressible, resilient, non-irritating to the wearer's skin and capable of absorbing and containing body fluids. The absorbent core 28 may be manufactured from a wide variety of liquid absorbent materials commonly used in disposable sanitary napkins, and other disposable absorbent articles. Examples of suitable absorbent materials include comminuted wood pulp (which is generally referred to as airfelt), creped cellulose wadding, modified cross-linked cellulose fibres (such as those described in U.S. Pat. No. 5,217,445 issued to Young, et al. on Jun. 8, 1993), capillary channel fibres (that is, fibres having intra-fibre capillary channels such as those described in U.S. Pat. No. 5,200,248 issued to Thompson, et al. on Apr. 6, 1993), absorbent foams (such as those described in U.S. Pat. No. 5,260,345, issued to DesMarais, et al. on Nov. 9, 1993 and U.S. Pat. No. 5,268,244 issued to DesMarais, et al. on Dec. 7, 1993), thermally bonded airlaid materials (such as those material described in U.S. patent application Ser. No. 08/141,156, entitled "Catamenial Absorbent Structures Having Thermally Bonded Layers For Improved Handling of Menstrual Fluids and Their Use In Catamenial Pads Having Improved Fit and Comfort" filed in the name of Richards, et al. on Oct. 21, 1993 (P&G Case 5051)), absorbent sponges, synthetic staple fibres, polymeric fibres, hydrogel-forming polymer gelling agents, peat moss, or any equivalent materials or combinations of materials. Suitable absorbent cores comprising foams are described in European Applications 0 598 833, 0 598 823 and 0 598 834.

The total absorbent capacity of the absorbent core 28 should be compatible with the intended body fluid loading for the sanitary napkin 20. Further, the absorbent capacity may be varied to accommodate wearers ranging in the expected amount of body fluid volume. For instance, a different absorbent capacity may be utilized for sanitary napkins intended for day time use as compared with those intended for night time use, or for sanitary napkins intended for use by teenage females as compared with those intended by more mature women.

According to a preferred embodiment of the present invention the absorbent core 28 of the sanitary napkin 20 is entirely constituted by a layer of compressed fibres 46 that performs the absorption of body fluids and is also intended for expanding the sanitary napkin 20 into the desired tridimensional structure while the sanitary napkin 20 is being worn. In the embodiment illustrated in FIGS. 1 to 3 the expansion and the final shaping of the sanitary napkin 20 into the tridimensional structure is provided by the swelling, substantially in Z-direction, of the material that constitutes the layer of compressed fibres 46 and that is activated during wear by the absorption of body fluids.

The fibres used for the compressed layer 46 of the present invention mainly comprise artificial, cellulose derived hydrophilic fibres. The fibres are substantially linear, that is, they are not curled, even though they may be slightly crimped in order to improve their processability. The fibres have a length of 10 to 70 mm, preferably of 40 to 50 mm, and a diameter of 1 to 20 dtex, preferably from 2 to 10 dtex. The fibres are air laid to form a layer of the desired basis weight, and then compressed to get a compressed layer having a thickness comprised, between 2 and 7 mm and a density that may range from 0.1 g/cc to 0.4 g/cc.

Materials selected for use as the layer of compressed fibres 46 are preferably compliant, comfortable and resilient in their dry, compressed state to enhance body fit and comfort of the sanitary napkin 20.

In a preferred embodiment of the present invention regenerated cellulose hydrophilic fibres prepared according to any well known method, e.g. the processing of pre-hydrolyzed sulphate chemical wood pulp to rayon by the viscose process, may be used for the layer 46.

Regenerated cellulose hydrophilic fibres with particular cross-sections that improve the pick up and delivery of fluids may also be used, e.g. fibres with a trilobal section or fibres with capillary channels formed therein, preferably on their exterior surfaces.

The density of the layer of compressed fibres 46 may be uniform throughout its entire surface, or may preferably vary either in longitudinal or in lateral direction, or in both. A layer of compressed fibres 46 having non uniform densities may be easily made e.g. by compressing to a uniform thickness a layer of fibres having zones with different basis weights, and therefore different thicknesses before compression.

In a preferred embodiment illustrated in FIGS. 1 to 3 the layer of compressed fibres 46 has a density that has its highest value at its centre and gradually decreases to a common minimum value towards both the longitudinal side margins and the transverse ends of the layer 46, so establishing a density gradient from the periphery to the centre of the layer of compressed fibres 46.

The fibres of the compressed layer 46 are completely unbonded or, alternatively, may be bonded with a binder prior to compression. Suitable binders are those that are water soluble; they may be used in such an amount that does not impair the subsequent swelling of the layer upon absorption of body fluids, preferably an amount not greater than 20% in weight.

Particles of absorbent gelling material may also be included within the layer of compressed fibres 46, preferably when it constitutes the absorbent core 28 of the sanitary napkin 20.

Natural fibres as cellulose or cotton fibres or synthetic fibres of the same length as the regenerated cellulose fibres, such as polyethylene, polypropylene or polyester fibres, may also be used in combination with the regenerated cellulose fibres to form the compressed layer 46, in an amount up to 50 weight %.

A layer of compressed regenerated cellulose fibres is capable of absorbing liquid very fast, with a rapid swelling in the direction of the compression; the swelling ratio is 2 to 10 times the dry thickness of the sheet.

In a preferred embodiment of the present invention, which is illustrated in FIGS. 1 and 2, a layer 46 of compressed regenerated cellulose fibres with a dry density of 0.125 g/cmc at its periphery which increases up to 0.2 g/cmc at its centre and a uniform thickness of 4 mm constitutes the absorbent core of the sanitary napkin 20. The layer 46 is 207 mm long and 64 mm wide. Suitable fibres for the layer 46 are regenerated cellulose linear fibres 40 mm long and with a thickness of 1.7 dtex, as those produced by Lenzing AG.

The layer of compressed regenerated cellulose fibres 46 is capable of absorbing body fluids quickly with a large increase in its volume, generally from about 2 to 10 times, and usually from 3 to 7 times its volume at the time of the compression; the volume increase depends on the density of the compressed layer: it is higher as the density of the layer of compressed fibres increases. The volume increase substantially corresponds to a swelling in the direction of the compression, that is in the Z-direction in the sanitary napkin 20.

The sanitary napkin 20 is produced and packaged as a conventional flat product, as illustrated in FIGS. 1 and 2. After the sanitary napkin 20 has been worn, as soon as the absorbed body fluids come in contact with the material of the layer of compressed fibres 46, this will begin to swell in Z-direction increasing its thickness, as can be seen in FIG. 3. Due to the density gradient that is preferably comprised in the layer of compressed fibres 46 the total swelling of the layer upon absorption of body fluids will not be uniform throughout its width and length, but will realize a profile that substantially follows the profile of the density gradient itself, that is, as illustrated in FIG. 3 with respect to the transverse dimension, the swelling will be higher at the centre of the layer 46, gradually decreasing towards the two longitudinal side margins. A similar configuration, not illustrated, will be achieved in longitudinal direction.

The topsheet 24 follows the swelling of the layer of compressed fibres 46 by straightening out the pleats or folds 52, therefore increasing its width without restraining the swelling.

After the absorption of body fluids and the subsequent swelling, the material of the layer of compressed fibres 46 is soft, compliant, conformable and resilient. It is compressible such that it will deform under the relatively small forces that are experienced during normal use. In addition to be compressible, the material of the layer of compressed fibres 46 is after swelling flexible and conformable such that it is able to provide improved fit through the topsheet 24 into and around the wearer's labia and perineum when the tridimensional structure is formed during the wearing time. The ability to follow the topography of the anatomy will provide intimate contact with the exposed genitalia of the female user. This helps provide better fluid transfer from the user into the layer of compressed fibres 46. While these characteristics of the layer of compressed fibres 46 allow for improved fit, they also cause the product to be both soft and comfortable for the wearer.

The swelling upon liquid absorption of the compressed fibres sponge material that forms the layer 46 creates a void volume that does not collapse in wet conditions and therefore enables the material to rapidly acquire further releases.

The swelling of the material forming the layer of compressed fibres 46 takes place only upon activation by the absorbed fluid, that is only during the use of the sanitary napkin 20 and in close contact with the user's anatomy; the formation of the tridimensional structure can therefore achieve a much better fit with the anatomy of the user. Moreover, the swelling of the layer of compressed fibres 46 may start where it is actually reached by the fluid first; the formation of the tridimensional structure may also fit, therefore, the different possible ways in which the body fluids may be released by various users.

The expanding topsheet 24 also provides a comfortable contact with the user's anatomy, without restraining the expansion of the sanitary napkin into the desired tridimensional structure upon activation by body fluids.

The sanitary napkin of the present invention is flat prior to use, and may be therefore manufactured and packaged more easily than a conventional elasticated or preformed article. Since the tridimensional structure is formed only during the use, the sanitary napkin of the present invention is also easier to wear.

In an alternative embodiment of the present invention, the sanitary napkin 20 may have two flaps (not shown), each of which are adjacent to and extend laterally from the side edge of the absorbent core. The flaps are configured to drape over the edges of the wearer's panties in the crotch region so that the flaps are disposed between the edges of the wearer's panties and the wearer's thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment facing surface so that the flaps can be folded back under the panty and attached to the garment facing side of the panty. In this way, the flaps serve to keep the sanitary napkin properly positioned in the panty.

The flaps may be constructed of various materials including materials used for the topsheet 24, backsheet 26, combinations thereof, and may be a laminate having tissue in the centre. Further, the flaps may be a separate element attached to the main body of the sanitary napkin 20 or can comprise extensions of the topsheet 24 and/or backsheet 26. It is recommended, however, that the flaps have a liquid impervious backsheet to prevent body fluids which reach the flaps from soiling the edges of the wearer's panties.

Preferred flaps that are suitable or adaptable to the sanitary napkin 20 of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986.

Optionally, the sanitary napkin 20 may comprise components that naturally wrap the sides of a wearer's panties. Sanitary napkins having components that naturally wrap the sides of a wearer's panties suitable for use with the sanitary napkin 20 of the present invention are disclosed in U.S. patent application Ser. No. 08/096,121 entitled "Absorbent Article having Panty Covering Components that Naturally Wrap the Sides of Panties", filed Jul. 22, 1993, in the names of Lavash, et al and U.S. patent application Ser. No. 08/277, 733 entitled "Absorbent Articles Having Undergarment Covering Components with Zones of Extensibility", filed Jul. 20, 1994, in the names of Weinberger, et al.

Figure 4:
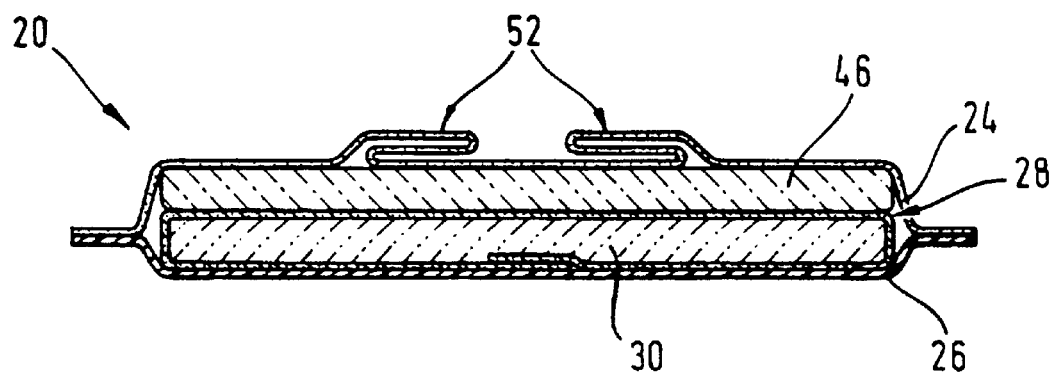
FIG. 4 is a cross-sectional view of another embodiment of a sanitary napkin according to the present invention.
Figure 5:
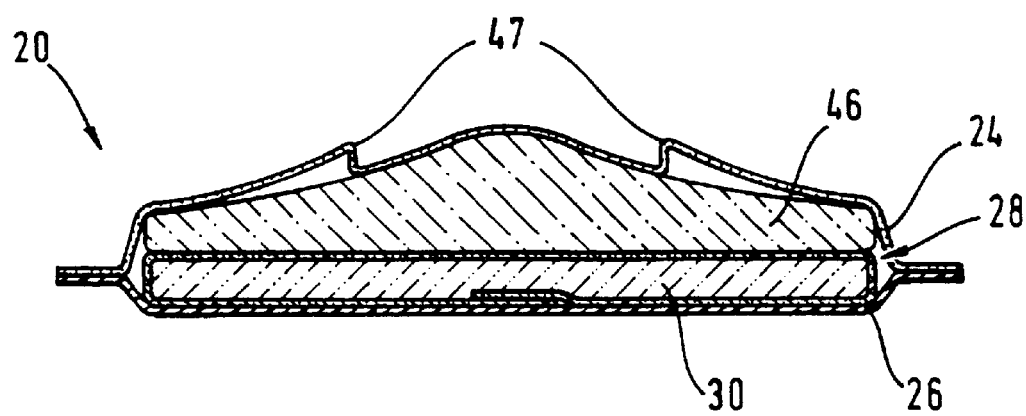
FIG. 5 is a cross-sectional view similar to that of FIG. 2, showing the sanitary napkin expanded into a tridimensional structure after activation during wear.

In an alternative embodiment illustrated in FIGS. 4 and 5 a sanitary napkin 20 similar to that illustrated in FIGS. 1 and 2 has an absorbent core 28 that comprises a further, substantially non-expanding absorbent element positioned between the layer of compressed fibres 46 and the backsheet 26. In the embodiment illustrated in FIGS. 4 and 5, this absorbent element is comprised of an absorbent layer 30 made of a thermally bonded airlaid material longitudinally folded twice on itself and comprising particles of absorbent gelling material therebetween, which are not shown for clarity.

The layer of compressed fibres 46 preferably forms at least part of the body facing surface of the absorbent core 28.

In the embodiment illustrated in FIGS. 4 and 5 the layer of compressed fibres 46 is positioned over the substantially non-expanding absorbent layer 30, in face to face relationship with it; it has the same length and width as the absorbent layer 30; alternatively, it can be smaller than the absorbent layer 30, either in width, or in length, or both, being preferably centered about the longitudinal and transverse centrelines O—O and A—A.

In the alternate embodiment shown in FIGS. 4 and 5 the total absorbent capacity of the sanitary napkin 20 is substantially provided for by the combination of the layer of compressed fibres 46 with the substantially non-expanding absorbent layer 30; the layer of compressed fibres 46 may be therefore suitably dimensioned, in length, width, thickness and densities, to get, in combination with the substantially non-expanding absorbent layer 30, the desired absorbent capacity for the sanitary napkin 20.

As illustrated in FIG. 4, the pleats or folds 52 of the topsheet 24 are positioned at both sides of the longitudinal centreline O—O and substantially parallel to it, but, differently from what is shown in FIG. 2, in each pleat or fold 52 the topsheet 24 is folded twice on itself toward the longitudinal centreline O—O of the sanitary napkin 20. During the swelling of the layer of compressed fibres 46 upon fluid absorption the straightening out of the pleats or folds 52 forms a sort of longitudinally oriented side cuffs 47 that provide a better seal against side leakage, as illustrated in FIG. 5; the side cuffs 47 may still be present when the swelling of the layer of compressed fibres 46 is completed if the overall width of the topsheet 24 is slightly higher than that which would be necessary to follow the complete swelling of the compressed regenerated cellulose sponge sheet 46.

In a further alternative embodiment, which is not illustrated, the sanitary napkin 20 may also comprise an acquisition layer or secondary topsheet positioned e.g. between the topsheet 24 and the absorbent core 28. The acquisition layer may serve several functions including improving wicking of body fluids over and into the underlying layers. By improving the wicking of body fluids, the acquisition layer provides a more even distribution of the body fluids throughout the underlying layers.

The acquisition layer can be positioned in the sanitary napkin 20 in any suitable position, as it is apparent to the man skilled in the art, but in any case it must be free to follow the expansion of the layer of compressed fibres 46 upon absorption of liquid, without restraining its swelling.

The acquisition layer preferably comprises materials that are capable of acquiring liquid very fast, and subsequently release it to underlying layers with substantially no retention capacity; suitable materials include nonwoven or woven webs of synthetic fibres including polyester, polypropylene, or polyethylene; natural fibres including cotton or cellulose; blends of such fibres; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al.

What is claimed is:

1. A sanitary napkin to be worn by a female user adjacent to her pudendal region, the sanitary napkin having a longitudinal centerline and a lateral centerline orthogonal thereto and defining longitudinal and lateral directions, respectively, the sanitary napkin further having a Z-direction which is orthogonal to both the longitudinal and the lateral directions, the sanitary napkin further comprising a liquid pervious topsheet, a backsheet joined to the topsheet, and an absorbent core intermediate the topsheet and the backsheet, the absorbent core comprising a body faceable surface, the sanitary napkin being substantially flat prior to use, wherein the absorbent core comprises a layer of compressed, regenerated cellulose, linear fibers capable of expanding the sanitary napkin into a tridimensional structure while being worn by the user and having a dry density of from 0.1 g/cc to 0.4 g/cc, the expanding layer of compressed, cellulose, linear fibers having a thickness of between 2 mm to 7 mm, and the expanding layer of compressed, cellulose, linear fibers being activateable by body fluids from the female user.

2. The sanitary napkin of claim 1 wherein the layer of compressed, cellulose, linear fibers provides the sanitary napkin with a substantially convex upward configuration.

3. The sanitary napkin of claim 1 wherein the topsheet is capable of expanding as the sanitary napkin expands upon activation by body fluids.

4. The sanitary napkin of claim 3 wherein the topsheet has at least a pleat or fold.

5. The sanitary napkin of claim 1 wherein the layer of compressed, cellulose, linear fibers upon activation by body fluids expands substantially in the Z-direction to provide the tridimensional structure.

6. The sanitary napkin of claim 1 wherein the layer of compressed, cellulose, linear fibers forms at least part of the body faceable surface of said absorbent core.

7. The sanitary napkin of claim 1 wherein the regenerated cellulose fibers have a length of 10 mm to 70 mm and a diameter of from 1 dtex to 20 dtex.

* * * * *